(12) United States Patent
Nishiyama et al.

(10) Patent No.: US 9,107,918 B2
(45) Date of Patent: Aug. 18, 2015

(54) METHOD FOR DETERMINING SENSITIVITY TO IRINOTECAN AND USE THEREOF

(75) Inventors: Masahiko Nishiyama, Iruma-gun (JP); Keiko Hiyama, Iruma-gun (JP); Keiji Tanimoto, Iruma-gun (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 170 days.

(21) Appl. No.: 13/203,810

(22) PCT Filed: Mar. 12, 2010

(86) PCT No.: PCT/JP2010/001772
§ 371 (c)(1),
(2), (4) Date: Aug. 29, 2011

(87) PCT Pub. No.: WO2010/103851
PCT Pub. Date: Sep. 16, 2010

(65) Prior Publication Data
US 2012/0129880 A1   May 24, 2012

(30) Foreign Application Priority Data

Mar. 13, 2009   (JP) .................................. 2009-061455

(51) Int. Cl.
| | | |
|---|---|---|
| C12Q 1/68 | (2006.01) | |
| C12P 19/34 | (2006.01) | |
| A61K 31/4745 | (2006.01) | |
| G01N 33/574 | (2006.01) | |
| C07H 21/02 | (2006.01) | |

(52) U.S. Cl.
CPC .......... *A61K 31/4745* (2013.01); *C12Q 1/6809* (2013.01); *C12Q 1/6886* (2013.01); *G01N 33/57419* (2013.01); *G01N 33/57484* (2013.01); *C12Q 2600/106* (2013.01); *C12Q 2600/158* (2013.01); *G01N 2333/4703* (2013.01); *G01N 2333/916* (2013.01); *G01N 2333/96466* (2013.01); *G01N 2333/988* (2013.01); *G01N 2800/52* (2013.01)

(58) Field of Classification Search
CPC ............. A61K 31/4745; C12Q 1/6809; C12Q 1/6886; C12Q 2600/106; C12Q 2600/158; G01N 2800/52; G01N 33/57419; G01N 33/57484
See application file for complete search history.

(56) References Cited

U.S. PATENT DOCUMENTS

2008/0076134 A1   3/2008 Muraca
2009/0143236 A1   6/2009 Inazawa et al.

FOREIGN PATENT DOCUMENTS

WO   2005 078100   8/2005

OTHER PUBLICATIONS

Narahara N. et al. 'Pharmacogenomic analysis for individual response to CPT-11 in colorectal cancer: Prediction formula of tumor response using novel marker genes and genotypes associated with the toxicity' Journal of Clinical Oncology, 2006 ASCO Annual Meeting Proceedings (Post-Meeting Edition). vol. 24, No. 18S (Jun. 20 Supplement), 2006: 2060.*
Sugimoto N.. et al. Annals of Oncology, vol. 17, Supplement 9, Sep. 2006, p. ix247.*
Perren Cobb, J. et al. Crit Care Med 2002 vol. 30, No. 12, pp. 2711-2721.*
Hoshikawa Y. et al. Physiol Genomics 12: 209-219, 2003.*
Chen G. et al. Molecular & Cellular Proteomics 1.4 (2002) pp. 304-313.*
Wong M.L. et al. BioTechniques (2005) vol. 39, No. 1, pp. 75-85.*
Introduction to Gene Expression—Getting Started Guide (2010), 36 pages from Applied Biosystems by Life Technologies.*
Extended Search Report issued Oct. 29, 2012 in European Application No. 10750607.3.
Masahiko Nishiyama, et al., "Pharmacokinetics and pharmacogenomics in gastric cancer chemotherapy", Advanced Drug Delivery Reviews, vol. 61, 2009, pp. 402-407.
Shimokuni, T. et al., "Chemosensitivity Prediction in Esophageal Squamous Cell Carcinoma: Novel Marker Genes and Efficacy-Prediction Formulae Using Their Expression Data", International Journal of Oncology, vol. 28, pp. 1153-1162, (2006).
Tanaka, T. et al., "Concise Prediction Models of Anticancer Efficacy of 8 Drugs Using Expression Data From 12 Selected Genes", International Journal of Cancer, vol. 111, pp. 617-626, (2004).
Fumoto, S. et al., "Selection of a Novel Drug-Response Predictor in Esophageal Cancer: A Novel Screening Method Using Microarray and Identification of IFITM1 as a Potent Marker Gene of CDDP Response", International Journal of Oncology, vol. 32, pp. 413-423, (2008).
Del Rio, M. et al., "Gene Expression Signature in Advanced Colorectal Cancer Patients Select Drugs and Response for the Use of Leucovorin, Fluorouracil, and Irinotecan", Journal of Clinical Oncology, vol. 25, No. 7, pp. 773-780, (Mar. 1, 2007).
Fumoto, S. et al., "Shokudo Gan Ni Okeru Koganzai Koka Yosoku System No Kaihatsu", Dai 64 Kai Nihon Gan Gakkai Gakujutsu Sokai Kiji, pp. 90-91, (2005), Pa1-0102.
Walther, A. et al., "Genetic Prognostic and Predictive Markers in Colorectal Cancer", Nature Reviews Cancer, vol. 9, pp. 489-499, (Jun. 18, 2009).
Kawato, Y. et al., "Intracellular Roles of SN-38, a Metabolite of the Camptothecin Derivate CPT-11, in the Antitumor Effect of CPT-11", Cancer Research, vol. 51, pp. 4187-4191, (Aug. 1991).

(Continued)

*Primary Examiner* — Stephen Kapushoc
(74) *Attorney, Agent, or Firm* — Oblon, McClelland, Maier & Neustadt, L.L.P.

(57) ABSTRACT

To provide a method for determining the sensitivity of a patient to irinotecan, SN-38, and/or a salt thereof, which method can determine the therapeutic response of the patient and to provide a novel cancer therapeutic means employing the method.

The method for determining the sensitivity of a subject to irinotecan, SN-38, and/or a salt thereof includes measuring the expression levels of AMD1 gene, CTSC gene, EIF1AX gene, C12orf30 gene, DDX54 gene, PTPN2 gene, and TBX3 gene in a specimen, and calculating the best tumor response rate (%), overall survival (days), or progression-free survival (days) from formulas (1) to (3).

7 Claims, 7 Drawing Sheets

(56) References Cited

OTHER PUBLICATIONS

Cecchin, E. et al., "Carboxylesterase Isoform 2 mRNA Expression in Peripheral Blood Mononuclear Cells is a Predictive Marker of the Irinotecan to SN38 Activation Step in Colorectal Cancer Patients", Clinical Cancer Research, vol. 11, No. 19, pp. 6901-6907, (Oct. 3, 2005).

Sorensen, N. M. et al., "TIMP-1 Is Significantly Associated With Objective Response and Survival in Metastatic Colorectal Cancer Patients Receiving Combination of Irinotecan, 5-Fluorouracil, and Folinic Acid", Clinical Cancer Research, vol. 13, No. 14, pp. 4117-4122, (Jul. 18, 2007).

Paradiso, A. et al., "Topoisomerase-I, Thymidylate Synthase Primary Tumour Expression and Clinical Efficacy of 5-FU/CPT-11 Chemotherapy in Advanced Colorectal Cancer Patients", Int. J. Cancer, vol. 111, pp. 252-258, (2004).

International Search Report Issued Apr. 6, 2010 in PCT/JP10/001772 filed Mar. 12, 2010.

\* cited by examiner

METHOD FOR DETERMINING SENSITIVITY TO IRINOTECAN AND USE THEREOF

CROSS-REFERENCE TO RELATED APPLICATIONS

The present application is a 35 U.S.C. §371 National Stage patent application of International patent application PCT/JP2010/001772, filed on Mar. 12, 2010, which claims priority to Japanese patent application JP 2009-061455, filed on Mar. 13, 2009.

TECHNICAL FIELD

The present invention relates to a sensitivity determining method for judging whether or not cancer has a therapeutic response to irinotecan, SN-38, and/or a salt thereof, and to use thereof.

BACKGROUND ART

Anticancer agents have various types such as an alkylating agent, a platinum agent, an antimetabolite, an anticancer antibiotic, and an anticancer plant alkaloid. These anticancer agents are effective for some cancers but not effective for other cancers. Even when an anticancer agent is confirmed to be effective for a certain cancer, the anticancer agent is effective for some patients and not effective for other patients. The parameter showing whether or not the anticancer agent exhibits the effect on the cancer of a specific patient is called sensitivity to the anticancer agent.

Irinotecan hydrochloride (CPT-11) is an anticancer agent which has been developed in Japan and which has an action mechanism based on the inhibition of topoisomerase I. In Japan, CPT-11 indicated for non-small-cell lung cancer, small-cell lung cancer, cervical cancer, and ovarian cancer was approved as an effective drug in January 1994. Further, CPT-11 indicated for gastric cancer, colorectal cancer, breast cancer, squamous cell carcinoma, and malignant lymphoma was approved in July 1995. CPT-11 in multi-drug therapy has been recognized to be one of standard chemotherapy, in particular, as a first line drug or a second line drug for colorectal cancer all over the world, and the efficacy of CPT-11 has been established.

Meanwhile, clinical performance including survival rate attained by chemotherapy of advanced or metastatic colorectal cancer has been drastically improved through a combination therapy employing a key drug such as CPT-11 or oxaliplatin, which was developed in 1990s, and a fluoropyrimidine drug such as fluorouracil (5-FU), which had been a main drug for the therapy of colorectal cancer. However, the response rate of such chemotherapy is as low as about 50%. That is, the chemotherapy is not effective for half of the patients to whom an anticancer agent has been administered with high risks such as serious adverse events. Thus, there is urgent demand for establishing a method for predicting the sensitivity of a patient to an anticancer agent, which method enables determination of therapeutic response of individual patients (i.e., indication of a responder or non-responder).

Generally, the therapy schedule of cancer chemotherapy requires a long period of time. After repetition of several courses of chemotherapy while emergence of adverse events is monitored, attainment of a therapeutic effect and continuation of the therapy are assessed. The assessment requires a long period of time and high medical cost, and the adverse events have actually been observed to a certain degree. Thus, if there were means for predicting whether or not individual patients can receive the effect of chemotherapy before or in an early stage of the therapy, the burden of the patients and emergence of adverse events can be reduced or mitigated, leading to reduction in medical cost.

Although CPT-11 itself has antitumor activity, CPT-11 is activated by carboxyl esterase in the body, to thereby form 7-ethyl-10-hydroxycamptothecin (SN-38), which has 100 to several thousand times stronger antitumor activity compared to that of CPT-11. Co-presence of CPT-11 and SN-38 in the body is thought to provide an antitumor effect. In hepatocytes, SN-38 is glucuronidated by UDP-glucuronosyltransferase (UGT), to thereby form SN-38 glucuronate conjugate (SN-38G) having no cytotoxicity. SN-38G is excreted mainly to bile and then transferred to the intestinal tract, and finally excreted to feces. A portion of SN-38G excreted to the intestinal tract is deconjugated by β-glucuronidase of enteric bacteria, to thereby form active SN-38 again. The thus-formed SN-38 is metabolized and excreted via the steps of re-absorption by the mediation of a transporter present at the intestinal tract epithelium, enterohepatic circulation, glucuronidation by UGT in intestinal epithelial cells, and the like (Non-Patent Document 1). In the course of this metabolism, SN-38 damages the intestinal mucosa, to thereby possibly induce diarrhea. Also, some studies revealed that SN-38 adversely affects bone marrow, where active cell division occurs, to thereby induce erythrocytopenia, leukocytopenia, and thrombocytopenia.

One cause for adverse effects such as serious diarrhea and neutropenia was confirmed to be a change in exposure amount of SN-38 in the body caused by genetic polymorphism of UGT1A1. However, regarding therapeutic effects, there has been no report that the therapeutic effect can be predicted on the basis of pharmacokinetics, due to the complexity in vivo pharmacokinetics of CPT-11, which include conversion of CPT-11 (pro-drug) to SN-38 (active metabolite) and detoxication thereof; re-generation of SN-38 in the course of enterohepatic circulation; and metabolism of CPT-11 and formation of SN-38 from the metabolite thereof. Meanwhile, it has been reported that the carboxylesterase mRNA expression level in peripheral blood mononuclear cells correlates with the AUC ratio of SN-38 to SN-38G but does not correlate with the tumor regression effect (Non-Patent Document 2).

There have also been reported the following factors relating to the sensitivity or resistance to CPT-11: mutation of topoisomerase I, which is a target of SN-38, and expression level thereof; activity of carboxylesterase, the enzyme involved in conversion of CPT-11 to SN-38; ABC transporter genes (multidrug resistance protein (MRP)-1, MRP-2, and breast cancer resistant protein (BCRP)/ABCG2), which affects the intracellular accumulation amounts of CPT-11 and SN-38; and BCL2 family genes (Patent Document 1). Studies have been conducted on correlations of cell proliferation antigen Ki-67, tumor suppressor gene TP53, etc. with response to CPT-11 therapy. Recently, a clinical study has revealed that the plasma level of tissue inhibitor of metalloproteinase-1 (TIMP-1), the TIMP-1 having anti-apoptosis action, is significantly correlated with the clinical prognosis of a metastatic colorectal cancer patient having undergone CPT-11+5-FU combination therapy (Non-Patent Document 3). As described above, many studies have been carried out on CPT-11-sensitivity predicting biomarkers and sensitivity prediction methods, due to their necessity. However, a study has revealed that neither topoisomerase I (target) nor thymidylate synthase (possible 5-FU-sensitivity predicting factor) has clear correlation with therapeutic response in 5-FU+CPT-11 combination therapy (Non-Patent Document 4). Therefore, no biomarker or sensitivity prediction method which definitely predicts therapeutic response has been established.

PRIOR ART DOCUMENT

Patent Documents

Patent Document 1: WO 2005/78100

Non-Patent Documents

Non-Patent Document 1: Cancer Res. 1991; 51: 4187-4191
Non-Patent Document 2: Clin. Cancer Res. 2005; 11: 6901-6907
Non-Patent Document 3: Clin. Cancer Res. 2007; 13: 4117-4122
Non-Patent Document 4: Int. J. Cancer 2004; 111: 252-258

SUMMARY OF THE INVENTION

Problems to be Solved by the Invention

An object of the present invention is to provide a method for determining the sensitivity of a patient to irinotecan, SN-38, and/or a salt thereof, which method can determine the therapeutic response of the patient. Another object is to provide a novel cancer therapeutic means employing the method.

Means for Solving the Problems

In view of the foregoing, the present inventors have thoroughly investigated, by use of cultured human cancer cells, gene expression upon addition of SN-38 thereto and sensitivity to SN-38, whereby genes conceivably involved in the sensitivity were specified. Then, human clinical tests were performed under sole administration of CPT-11, to thereby investigate a method for determining the sensitivity of a patient to CPT-11 by use of the specified genes. As a result, the present inventors have found that the sensitivity parameters of a patient to irinotecan, SN-38, and/or a salt thereof; specifically, the best tumor response rate (%), overall survival (days), and progression-free survival (days), can be calculated by inputting the expression levels of the seven genes to a specific calculation formula. On the basis of this finding, the inventors have further investigated, and have found that, by determining the gene expression levels of a biosample derived from a cancer patient and inputting the levels to the calculation formula, whether or not the cancer of the cancer patient has sensitivity to irinotecan, SN-38, and/or a salt thereof can be determined; that, by employing an increase in value obtained from the calculation formula as an index, a sensitivity-enhancing agent can be selected through screening; and that, by employing the sensitivity-enhancing agent in combination with irinotecan, SN-38, and/or a salt thereof which are the targets of sensitivity enhancement, the therapeutic effects of the anticancer agent can be remarkably enhanced. The present invention has been accomplished on the basis of these findings.

Accordingly, the present invention provides a method for determining the sensitivity of a subject to irinotecan, SN-38, and/or a salt thereof, the method comprising measuring the expression levels of AMD1 gene, CTSC gene, EIF1AX gene, C12orf30 gene, DDX54 gene, PTPN2 gene, and TBX3 gene in a specimen, and calculating the best tumor response rate (%), overall survival (days), or progression-free survival (days) from the following formulas (1) to (3):

Best tumor response rate (%)=139.49−12.089×A−84.477×B−12.737×C+85.900×D−29.119×E−6.8630×F+20.303×G (1);

Overall survival (days)=512.78−192.11×A−120.78×B+134.53×C−11.883×D+157.24×E+31.962×F−386.55×G (2); and Progression-free survival (days)=68.076+78.277×A−57.358×B−15.011×C+8.9798×D+73.077×E−38.961×F−43.313×G (3)

(wherein A represents an expression level of AMD1 gene; B represents an expression level of CTSC gene; C represents an expression level of EIF1AX gene; D represents an expression level of C12orf30 gene; E represents an expression level of DDX54 gene; F represents an expression level of PTPN2 gene; and G represents an expression level of TBX3 gene).

The present invention also provides a kit for determining the sensitivity of a subject to irinotecan, SN-38, and/or a salt thereof, wherein the kit comprises (A) assay reagents for measuring the expression levels of the seven genes, and (B) a protocol for calculating the best tumor response rate (%), overall survival (days), or progression-free survival (days) from the formulas (1) to (3).

The present invention also provides a method for screening a sensitivity-enhancing agent to irinotecan, SN-38, and/or a salt thereof, the method comprising measuring the expression levels of AMD1 gene, CTSC gene, EIF1AX gene, C12orf30 gene, DDX54 gene, PTPN2 gene, and TBX3 gene in a specimen, and employing, as an index, an increase in any one of the best tumor response rate (%), overall survival (days), or progression-free survival (days) obtained from the formulas (1) to (3).

The present invention also provides a sensitivity-enhancing agent to irinotecan, SN-38, and/or a salt thereof obtained through the screening method.

The present invention also provides a composition for cancer therapy comprising the sensitivity-enhancing agent and irinotecan, SN-38, and/or a salt thereof.

Effects of the Invention

According to the method of the present invention for determining the sensitivity of a subject to irinotecan, SN-38, and/or a salt thereof, the anticancer agent therapeutic response of a patient can be determined before administration or in an early stage after administration of the anticancer agent. As a result, an anticancer agent having higher therapeutic effect can be selected, and progression of cancer and aggravation of adverse effects, which results from continuous administration of an anticancer agent exerting no expected therapeutic effect, can be prevented. Thus, reductions in burden of the patient and medical cost can be expected. Through employment of the sensitivity determination method, a drug which enhances the sensitivity to irinotecan, SN-38, and/or a salt thereof can be selected through screening. By employing the sensitivity-enhancing agent in combination with irinotecan, SN-38, and/or a salt thereof, the cancer therapeutic effect can be remarkably enhanced.

MODES FOR CARRYING OUT THE INVENTION

Figure 1:
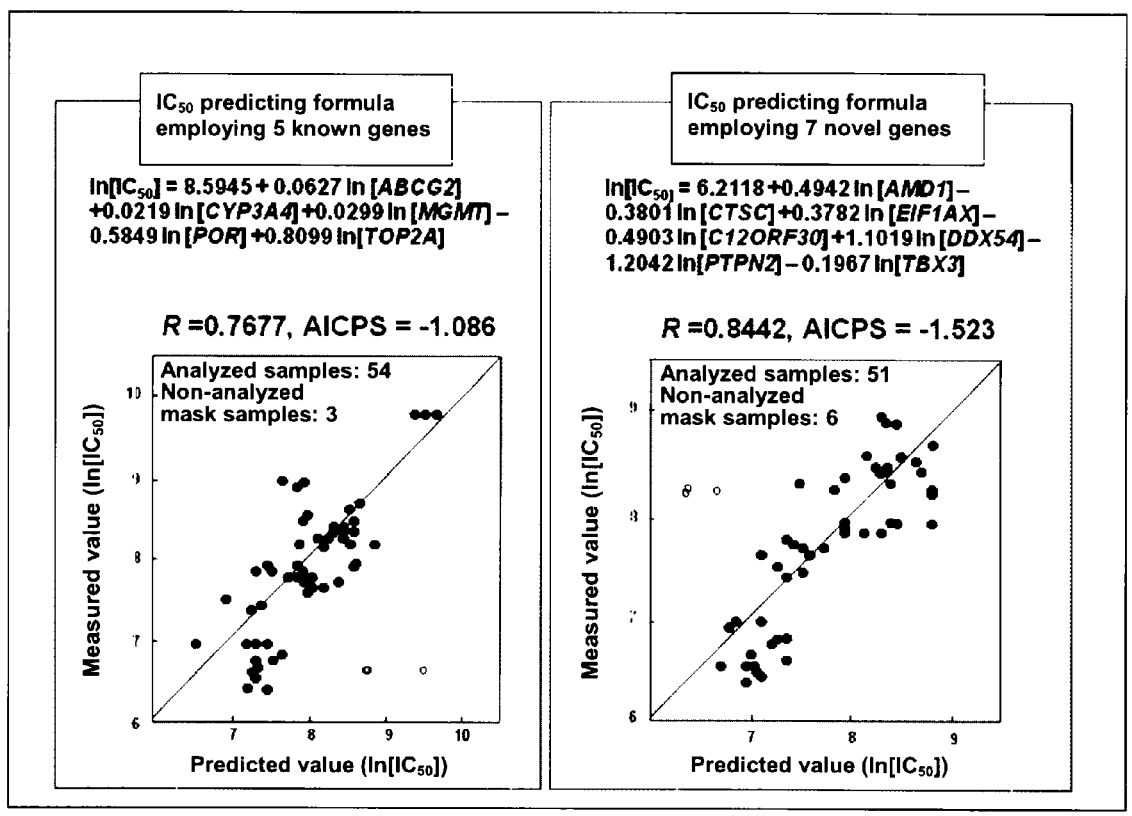
FIG. 1 A graph showing a formula for predicting the in vitro effect of SN-38, established from the expression levels of five known genes and seven novel genes.
Figure 2:
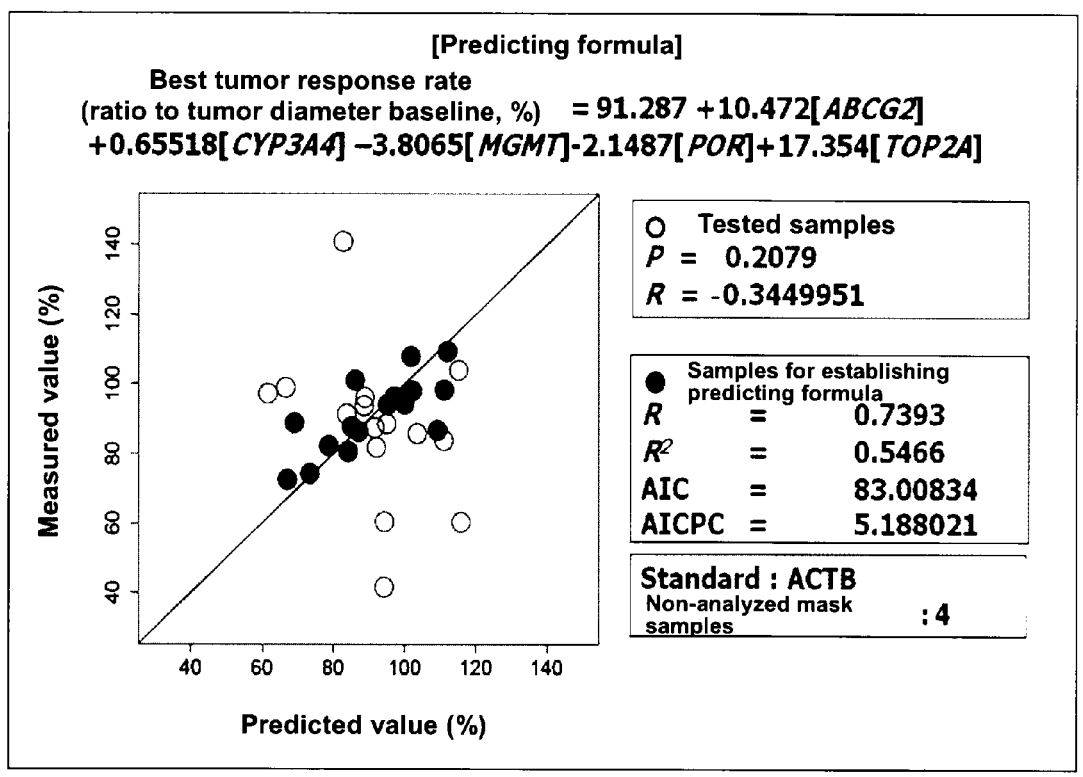
FIG. 2 A graph showing a formula for predicting the best tumor response rate (%) under sole administration of irinotecan, established from the expression levels of five known genes, and showing the limit of the prediction.
Figure 3:
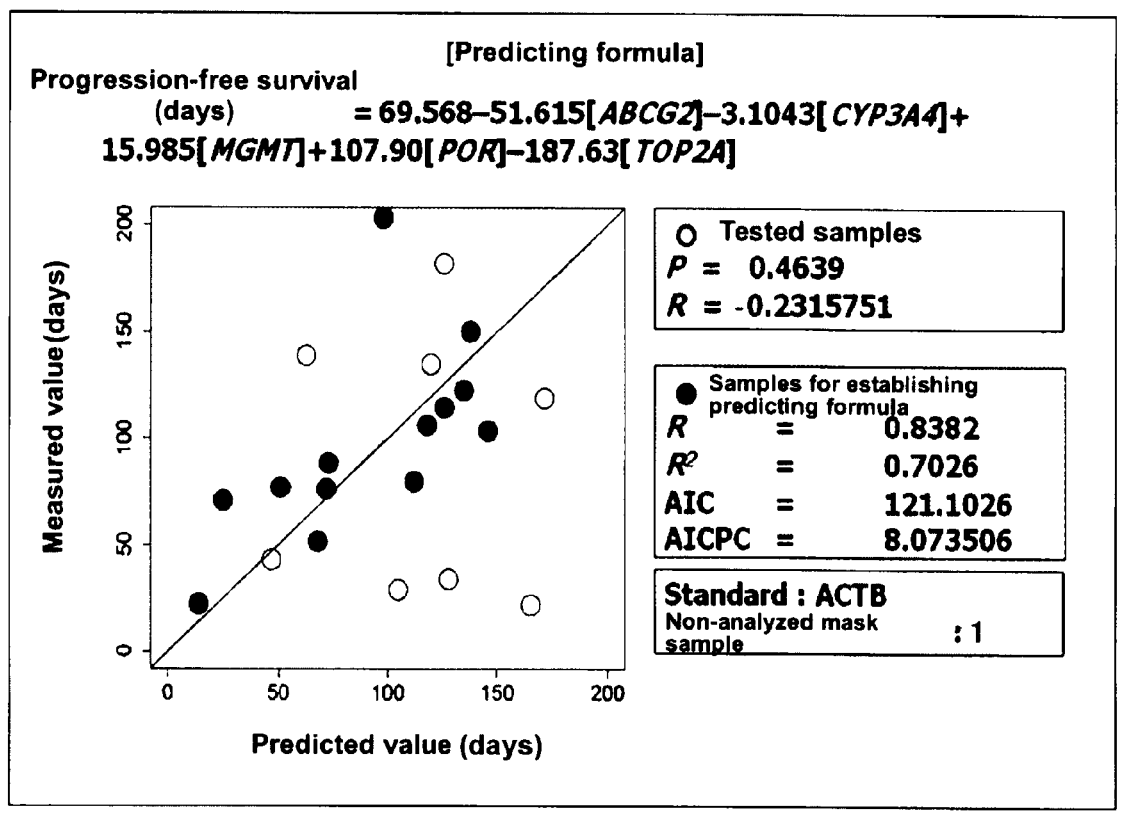
FIG. 3 A graph showing a formula for predicting the progression-free survival (days) under sole administration of irinotecan, established from the expression levels of five known genes, and showing the limit of the prediction.
Figure 4:
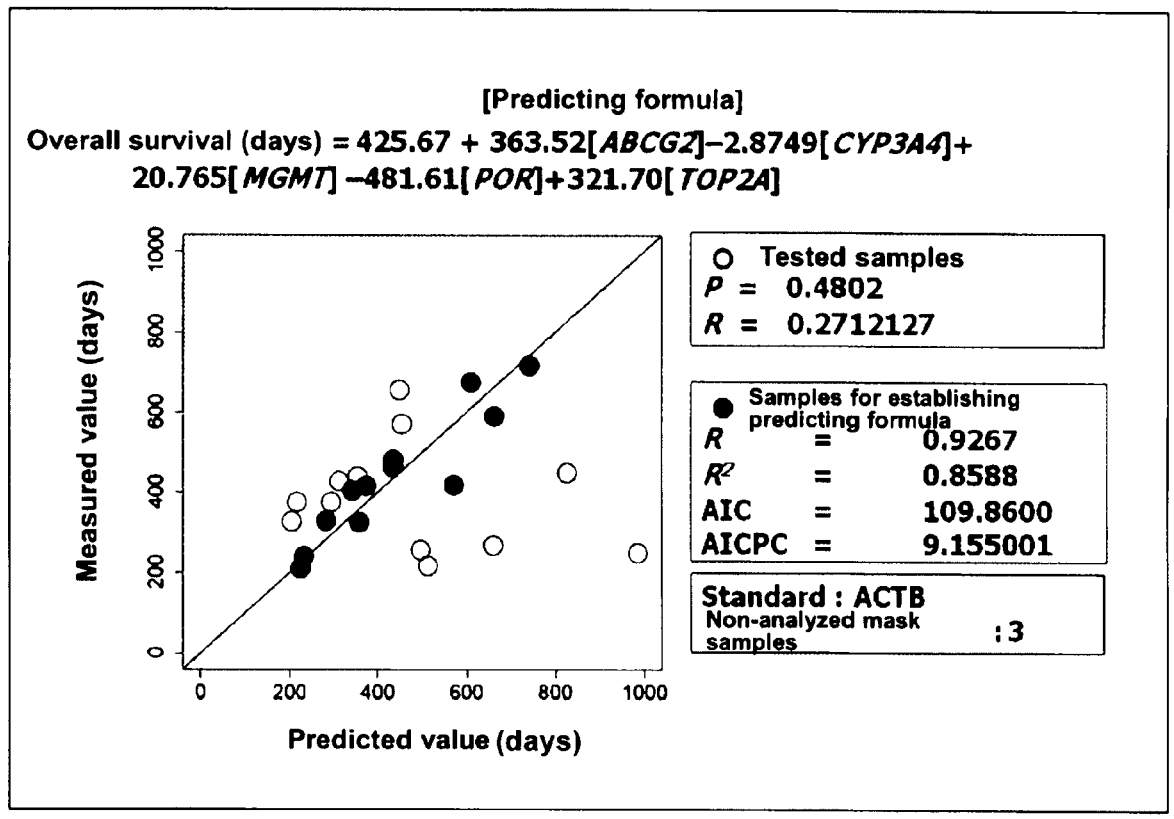
FIG. 4 A graph showing a formula for predicting the overall survival (days) under sole administration of irinotecan, established from the expression levels of five known genes, and showing the limit of the prediction.
Figure 5:
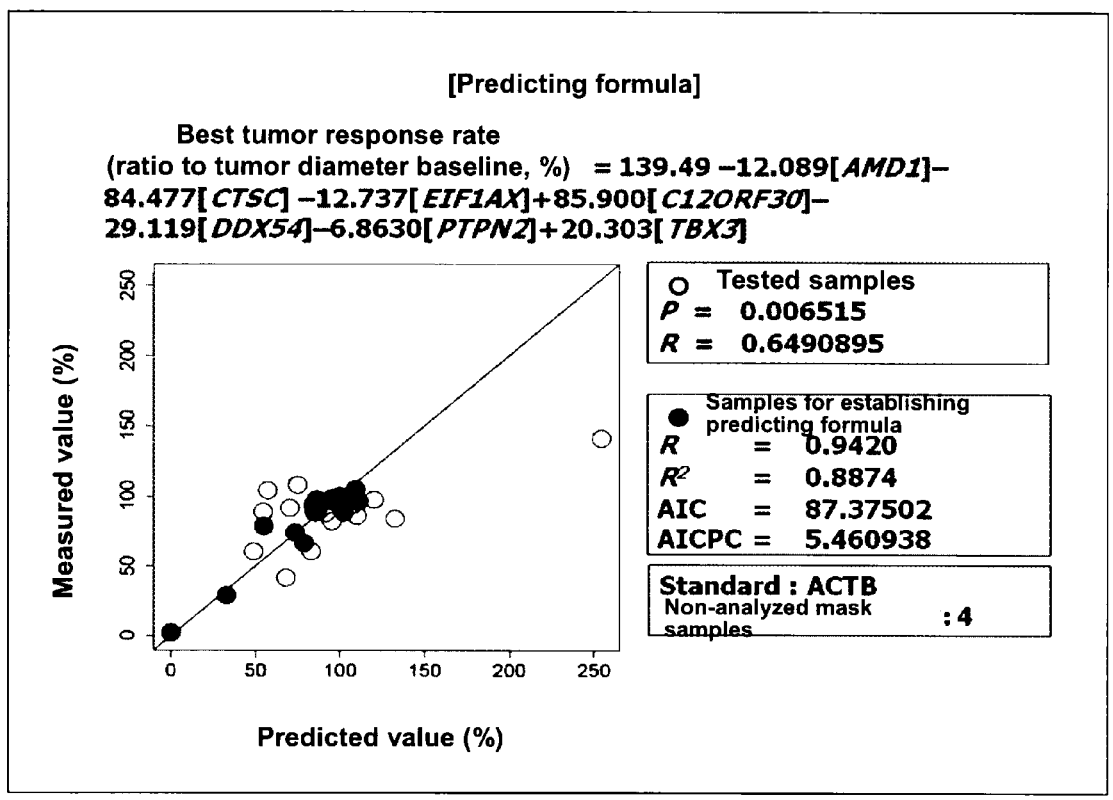
FIG. 5 A graph showing a formula for predicting the best tumor response rate (%) under sole administration of irinotecan, established from the expression levels of seven novel genes, and showing the utility of the prediction.
Figure 6:
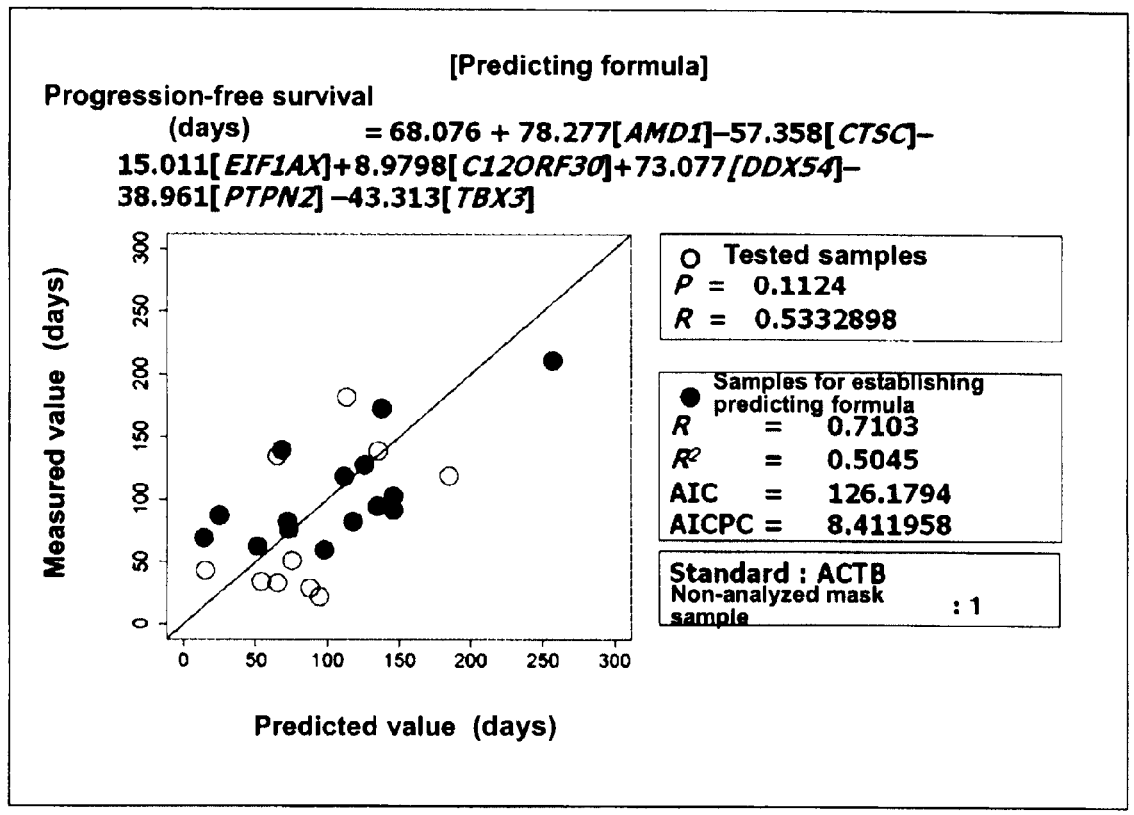
FIG. 6 A graph showing a formula for predicting the progression-free survival (days) under sole administration of irinotecan, established from the expression levels of seven novel genes, and showing the utility of the prediction.
Figure 7:
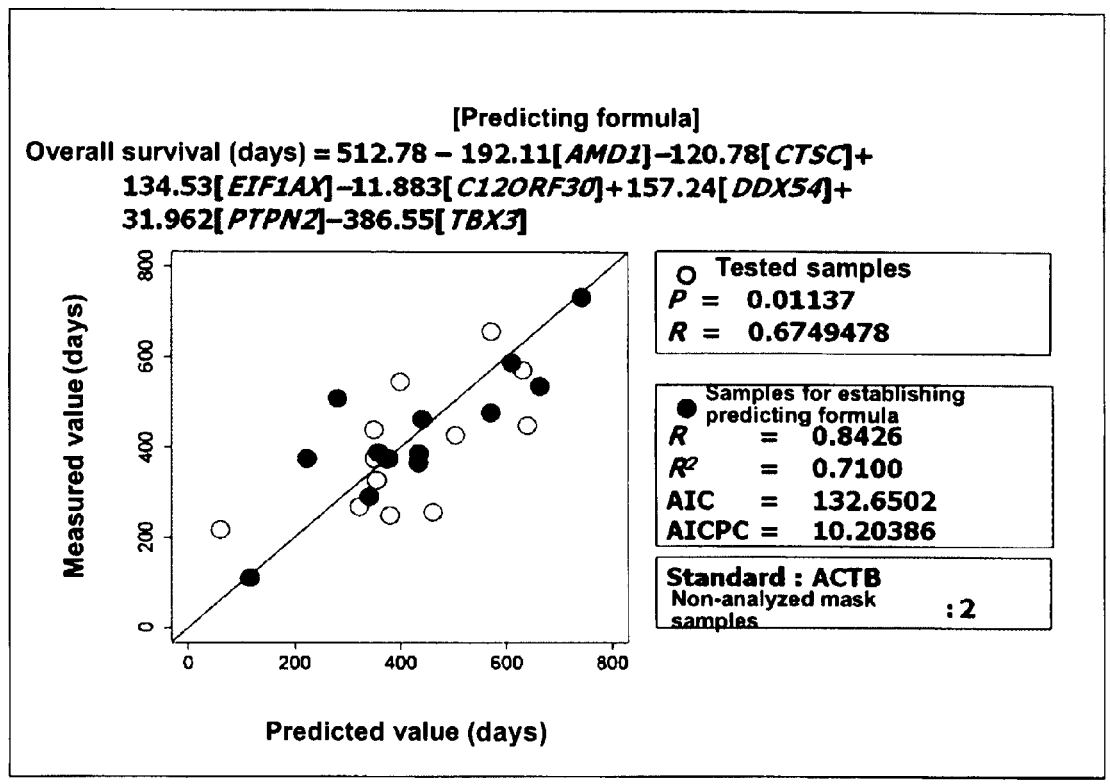
FIG. 7 A graph showing a formula for predicting the overall survival (days) under sole administration of irinotecan, established from the expression levels of seven novel genes, and showing the utility of the prediction.

The method of the present invention for determining the sensitivity of a subject to irinotecan, SN-38, and/or a salt thereof can be carried out by measuring the expression levels of the aforementioned seven genes in a specimen, and calculating the best tumor response rate (%), overall survival (days), or progression-free survival (days) by inputting the expression levels into the formulas (1) to (3). The seven genes employed in the present invention were previously thought to relate to the sensitivity to SN-38 in a system employing cultured human cancer cells. However, when the sensitivity of human subjects to CPT-11 was studied in actual clinical tests, each gene itself did not reflect the sensitivity to CPT-11. Thus, a multiple regression analysis was performed between the expression level of each gene in the specimens obtained in the clinical test and the best tumor response rate (%), overall survival (days), and progression-free survival (days) of the relevant patient (see Shimokuni T et al., "Chemosensitivity prediction in esophageal squamous cell carcinoma: novel marker genes and efficacy-prediction formulae using their expression data." Int. J. Oncol. 2006. 5.). The analysis has revealed that the values obtained by inputting the expression levels of the aforementioned seven genes into the formulas (1) to (3) have considerably high correlation to the best tumor response rate (%), overall survival (days), and progression-free survival (days). Therefore, through measuring the expression levels of the aforementioned seven genes in the specimen and inputting the measurements into the following formulas (1) to (3), the sensitivity of a subject to irinotecan, SN-38, and/or a salt thereof can be determined, whereby the best tumor response rate (%), overall survival (days), and progression-free survival (days) can be predicted.

$$\text{Best tumor response rate (\%)} = 139.49 - 12.089 \times A - 84.477 \times B - 12.737 \times C + 85.900 \times D - 29.119 \times E - 6.8630 \times F + 20.303 \times G \quad (1);$$

$$\text{Overall survival (days)} = 512.78 - 192.11 \times A - 120.78 \times B + 134.53 \times C - 11.883 \times D + 157.24 \times E + 31.962 \times F - 386.55 \times G \quad (2); \text{ and}$$

$$\text{Progression-free survival (days)} = 68.076 + 78.277 \times A - 57.358 \times B - 15.011 \times C + 8.9798 \times D + 73.077 \times E - 38.961 \times F - 43.313 \times G \quad (3)$$

(wherein A represents an expression level of AMD1 gene; B represents an expression level of CTSC gene; C represents an expression level of EIF1AX gene; D represents an expression level of C12orf30 gene; E represents an expression level of DDX54 gene; F represents an expression level of PTPN2 gene; and G represents an expression level of TBX3 gene).

In the present invention, AMD1 gene refers to a gene expressing mRNA having a nucleotide sequence defined by GenBank Accession No. NM_001634, or a homologue of the gene;

CTSC gene refers to a gene expressing mRNA having nucleotide sequences defined by GenBank Accession Nos. NM_148170 and NM_001814, or a homologue of the gene;

EIF1AX gene refers to a gene expressing mRNA having a nucleotide sequence defined by GenBank Accession No. NM_001412, or a homologue of the gene;

C12orf30 gene refers to a gene expressing mRNA having a nucleotide sequence defined by GenBank Accession No. NM_024953, or a homologue of the gene;

DDX54 gene refers to a gene expressing mRNA having a nucleotide sequence defined by GenBank Accession No. NM_024072, or a homologue of the gene;

PTPN2 gene refers to a gene expressing mRNA having nucleotide sequences defined by GenBank Accession Nos. NM_002828 and NM_080422, or a homologue of the gene; and TBX3 gene refers to a gene expressing mRNA having nucleotide sequences defined by GenBank Accession Nos. NM_005996 and NM_016569, or a homologue of the gene.

As used herein, the term "gene" refers not only to double strand DNA but also to single strand DNA forming the double strand DNA such as a sense strand or an antisense strand. No particular limitation is imposed on the length of the DNA. Examples of the nucleic acid (polynucleotide) include RNA and DNA. Specific examples of DNA include cDNA, genomic DNA, and synthetic DNA, and specific examples of RNA include mRNA, rRNA, and siRNA. The term "polynucleotide" also encompasses an oligonucleotide consisting of a plurality of nucleotides.

For carrying out the method of the present invention for determining the sensitivity of a subject to irinotecan, SN-38, and/or a salt thereof, the expression levels of the aforementioned seven genes in a specimen are measured, and the measurements are put into the formulas (1) to (3). Examples of the specimen include biosamples derived from a subject having cancer (cancer patient) such as blood, serum, plasma, urine, tumor tissue and cells, ascites, pleural fluid, cerebrospinal fluid, feces, and sputum. Among them, tumor tissue is particularly preferred. The specimen may be treated with an appropriate known method and employed as a tissue extract, a tissue preparation, etc.

Examples of the cancer to which the present invention is applied include lip, oral, and pharyngeal cancers, typically pharyngeal cancer; digestive cancers such as esophageal cancer, gastric cancer, and colorectal cancer; respiratory and intrathoracic organ cancers such as lung cancer; bone and articular cartilage cancers; malignant melanoma, squamous cell carcinoma, and other skin cancers; mesothelial and soft tissue cancers such as mesothelioma; female genital cancers such as breast cancer, uterine cancer, and ovarian cancer; male genital cancers such as prostate cancer; urinary tract cancers such as bladder cancer; eye, brain, and central nervous system cancers such as brain tumor; thyroid cancer and other endocrine cancers; lymphoid tissue, hematopoietic tissue, and other related tissue cancers such as non-Hodgkin's lymphoma and lymphoid leukemia; and metastatic cancers from the aforementioned cancers as primary foci. Among them, the present invention is preferably applied to non-small-cell lung cancer, small-cell lung cancer, cervical cancer, ovarian cancer, gastric cancer, colorectal cancer, squamous cell carcinoma, and malignant lymphoma, particularly preferably to colorectal cancer. Particularly preferably, the present invention is applied to cancer without chemotherapy.

The gene expression level may be measured by use of a probe or primer which can detect the genes of the present invention or mRNA thereof, whereby the copy number or expression level of a target gene is determined through the southern hybridization method, the DNA microarray method, the real-time PCR method, the RT-PCR method, or the like. Also, the polypeptide encoded by the gene may be employed as a target of measurement. Although no particular limitation is imposed on the measurement target, so long as the target reflects the gene expression level, mRNA of the target gene is preferably employed as a measurement target. As used herein, the "measurement of gene expression level" also encompasses confirmation of the presence of expression of the gene.

Hereinafter, the PCR method will be described in detail. In the case where mRNA is employed as a measurement target, if required, the specimen is subjected to known preliminary treatments such as filtration, centrifugation, and chromatographic treatment. Then, RNA can be extracted from the specimen through a generally employed method such as the guanidine-cesium chloride ultracentrifugation method, the acidic guanidine-phenol chloroform method (AGPC method), the magnetic beads method, or the silica column method. RNA extraction may also be performed by means of a commercial kit (QIAGEN RNeasy KIt, TRIZOL, etc.).

The mRNA level may be determined through, for example, (1) determining the amount of the amplification product obtained through PCR employing a nucleic acid fragment which can specifically hybridize with the target mRNA and an RNA derived from the specimen; (2) determining the hybridization efficiency between a nucleic acid fragment which can specifically hybridize with the target mRNA and an RNA derived from the specimen; or (3) other known quantitation methods.

In the case of PCR, the "nucleic acid fragment which can specifically hybridize with the target mRNA" may be designed by comparing the nucleotide sequence of the target gene with the nucleotide sequence of another gene and selecting a sequence specific to mRNA of the target gene. The nucleotide sequence of mRNA of the target gene may be obtained with reference to, for example, a database (e.g., GenBank). Alternatively, the nucleotide sequence is aligned by means of a software (e.g., Clustal X), and a specific sequence is visually selected. No particular limitation is imposed on the length of the nucleic acid fragment. However, a nucleic acid fragment consisting of 5 to 50 bases is preferred, with a nucleic acid fragment consisting of 18 to 25 continuous bases being more preferred.

The nucleic acid fragment which can hybridize with mRNA of the target gene is not limited to the thus-designed sequence, and those skilled in the art can conceive other equivalents on the basis of common technical sense. Such equivalents include a nucleic acid fragment having a nucleotide sequence complementary to the thus-designed sequence, and a nucleic acid fragment which has a nucleotide sequence homologous to any of the above sequences and which can be employed for determining the level of mRNA of the target gene. Examples of such equivalents include (a) a nucleic acid fragment which has a nucleotide sequence equivalent to the nucleotide sequence, except that 1 to 10, preferably 1 or several bases are substituted, added, or deleted; (b) a nucleic acid fragment which has a nucleotide sequence having an identity of 90% or higher, preferably 95% or higher, more preferably 99% or higher, to the nucleotide sequence; and (c) a nucleic acid fragment which has a nucleotide sequence which hybridizes, under stringent conditions, with the DNA fragment having a nucleotide sequence complementary to the nucleotide sequence.

The nucleic acid fragment may be a nucleic acid fragment in which any number, preferably 100 or less, more preferably 20 or less, even more preferably 10 or less of bases are added to one or two ends thereof, preferably to the 5' end.

The thus-designed nucleic acid fragment may be, for example, synthesized artificially, according to the nucleotide sequence thereof, by means of a DNA synthesizer. Preferably, the specificity of the nucleic acid fragment is confirmed after the synthesis. When the target mRNA is employed as a template, the specificity may be confirmed by the presence of a specific PCR amplicon, which is not obtained in the case of a certain reference.

In the case of AMD1 gene, examples of such nucleic acid fragments include a nucleic acid fragment having a part of the nucleotide sequence defined by GenBank Accession No. NM_001634 or having a nucleotide sequence complementary to the nucleotide sequence, and a nucleic acid fragment which has a nucleotide sequence homologous to any of the above sequences and which is functionally equivalent to the above nucleic acid fragment. Examples of the nucleic acid fragment which has a nucleotide sequence homologous to any of the above sequences and which is functionally equivalent to the above nucleic acid fragment include the following nucleic acid fragments (a) to (c) which can be employed for determining the level of mRNA of the target gene. The same is applied to the cases of genes other than AMD1 gene. Specific examples include (a) a nucleic acid fragment which has a nucleotide sequence equivalent to a part of the nucleotide sequence defined by GenBank Accession No. NM_001634 or a nucleotide sequence complementary to the nucleotide sequence, except that 1 or several bases are deleted, substituted, or added; (b) a nucleic acid fragment which has a nucleotide sequence having an identity of 90% or higher, preferably 95% or higher, more preferably 99% or higher, to a part of the nucleotide sequence defined by GenBank Accession No. NM_001634 or a nucleotide sequence complementary to the nucleotide sequence; and (c) a nucleic acid fragment which has a nucleotide sequence which hybridizes, under stringent conditions, with the DNA fragment having a part of the nucleotide sequence defined by GenBank Accession No. NM_001634 or a nucleotide sequence complementary to the nucleotide sequence.

The identity of a nucleotide sequence is calculated by means of a homology analysis program, GENETYX™.

The term "stringent conditions" refers to two DNA fragments being hybridized with each other under standard hybridization conditions as described by Sambrook J. et al. (Expression of cloned genes in E. coli (Molecular Cloning: A laboratory manual (1989)), Cold Spring Harbor Laboratory Press, New York, USA, 9.47-9.62 and 11.45-11.61).

The mRNA level of a specimen may be determined through PCR employing the thus-produced nucleic acid fragments and RNA derived from the specimen, preferably through real-time RT-PCR including a step of producing cDNA from mRNA. RT-PCR may be performed according to a known technique such as two-step RT-PCR or one-step RT-PCR. From the viewpoints of simplicity and prevention of cross-contamination, one-step RT-PCR is preferred. One-step RT-PCR may be performed by means of, for example, a commercial kit (e.g., QIAGEN One-Step RT-PCR kit). As the enzyme having reverse transcription activity which may be employed in RT reaction, a variety of reverse transcriptases such as M-MHV reverse transcriptase may be employed. The DNA polymerase, which is employed in PCR for amplifying a DNA fragment, preferably has heat resistance (≥90° C.)

In one mode of such PCR, thermal denaturation reaction (double strand DNA to single strand DNA) is performed at 90 to 98° C., annealing reaction for hybridizing a primer to template cDNA is performed at 37 to 72° C., and extension reaction in which DNA polymeraze acts is performed at 50 to 75° C. The set of reactions (cycle) is performed once to some tens of times. One preferred reaction conditions include thermal denaturation at 95° C. for 30 seconds, annealing at 60° C. for 30 seconds, and extension at 72° C. for 40 seconds. In PCR, two primers are preferably used in combination. In this case, the two primers must be selected so as to form a combination of a sense strand and an anti-sense strand. The nucleic acid fragment of the present invention may serve as a probe, and may be used in combination with other known universal primers, oligonucleotides, etc.

The specimen sample containing mRNA serving as a template for RT-PCR preferably has a total RNA amount of 1 pg to 1 μg, more preferably 2 ng to 50 ng.

When PCR has appropriately proceeded, the "PCR amplicon amount" and the "PCR cycle number" are generally correlated with the "PCR template amount." Thus, the mRNA level of a target gene; i.e., the target gene expression level, can be calculated from the amount of amplicon produced in PCR and the PCR cycle number.

No particular limitation is imposed on the method of determining the PCR amplicon amount and the PCR cycle number, and any method may be employed. For example, the PCR cycle number may be counted when the DNA level has reached a predetermined level. This procedure may be performed by, for example, determining the PCR cycle number when the fluorescence intensity has reached a predetermined level in a combinatory method including the PCR method in which a PCR amplicon is labeled and the PCR method in which the label is monitored with time. In one typical procedure, the labeling is performed by use of a fluorescent dye, and the label is monitored by measuring fluorescence intensity. In one mode of labeling with a fluorescent dye, an intercalater fluorescent dye such as SYBR(R) Green I may be employed. Since the intercalater dye enhances the fluorescence intensity via intercalation with a double-strand nucleic acid, a fluorescence intensity which correctly reflects the PCR amplicon level is obtained. Labeling with a fluorescent dye may also be accomplished by use of TaqMan probe, Moleculer Beacon, etc., which are labeled with a fluorescent dye. A TaqMan probe or Moleculer Beacon is a probe in which a fluorescent dye and a quencher are bonded to an oligonucleotide having a homology to an internal sequence of a region which is amplified through PCR. The probe is additionally employed in PCR. Since fluorescence in response to the degree of PCR is emitted through interaction between the fluorescent dye and the quencher bonded to the probe, the PCR product formed through amplification can be monitored by measuring the fluorescence intensity at each PCR stage.

As described above, the target gene mRNA level of a specimen may also be determined from, for example, the hybridization efficiency between the nucleic acid fragment which can hybridize specifically with a target mRNA and RNA derived from the specimen.

The nucleic acid fragment which can hybridize specifically with a target gene mRNA may be a nucleic acid fragment as designed and produced in the aforementioned manner. The nucleic acid fragment is preferably a labeled nucleic acid fragment. Examples of the labeling agent include an enzyme, a paramagnetic ion, biotin, a fluorescent dye, a chromophore, a heavy metal, and a radio-isotope. A more preferred marker is an enzyme. Examples of the enzyme include horse radish peroxidase and alkaline phosphatase. The labeling may be performed through a known method. Through determining the hybridization degree between a sample containing RNA derived from a specimen and the nucleic acid fragment, the target gene mRNA level of the specimen can be determined through a known calculation method. No particular limitation is imposed on the method of determining the degree of hybridization, and it may be determined according to a known method, for example, measuring a label bound to the nucleic acid fragment. That is, when a nucleic acid fragment labeled with a fluorescent dye is used, the fluorescence intensity is measured, for determining the degree of hybridization.

The expression level of a target gene may also be determined by use, as a probe, of a nucleic acid fragment which can specifically hybridize with a nucleotide sequence of the target gene or mRNA thereof. In the case of AMD1 gene, there may be used, as a probe, a nucleic acid fragment having a part of the nucleotide sequence defined by GenBank Accession No. NM_001634 (e.g., GCATGTGAGTGTTCCGACT-TCATCTGTTCC (SEQ ID NO: 1)) or having a nucleotide sequence complementary to the nucleotide sequence, or a nucleic acid fragment which has a nucleotide sequence homologous to any of the above sequences and which is functionally equivalent to the above nucleic acid fragment. These probes may be immobilized on any solid phase, to thereby provide a DNA chip, a gene chip, a cDNA microarray, an oligo DNA array, etc.

Other than the aforementioned probes, there may also be employed, as a probe, a combination of a plurality of nucleic acid fragments which are designed to specifically detect a nucleotide sequence of the target gene or mRNA thereof and which can specifically hybridize with plurality of regions appropriately selected from a nucleotide sequence of the target gene or mRNA thereof.

No particular limitation is imposed on the solid phase which is employed for immobilizing a probe, so long as the solid phase can immobilize polynucleotide. Examples of the solid phase include glass plate, nylon membrane, microbeads, a silicon chip, and a capillary. The solid phase may be labeled. No particular limitation is imposed on the labeling agent, and a fluorescent dye, a radio-isotope, etc. may be used. In immobilization of polynucleotide on a solid phase, a polynucleotide which has been synthesized in advance may be placed on a solid phase, or a target polynucleotide may be synthesized on a solid phase. When a DNA microarray is selected, immobilization may be performed by means of a commercial spotter or the like, through an appropriate known method (printing polynucleotide through ink-jet method, in situ synthesis, or photolithography) depending on the type of the probe to be immobilized.

The expression level of a target gene may be determined by hybridizing the aforeprepared DNA chip or the like with a labeled DNA or RNA prepared from an RNA obtained from a specimen (e.g., cultured cells, tissue, tissue section, or blood lysate) or a labeled DNA or RNA prepared directly from the specimen; and measuring, as a signal attributed to the labeled probe, the amount of the double-strand formed of the probe and the labeled DNA or RNA. The signal may be detected through a routine method, for example, by means of a radiation counter, a fluorescence detector, etc.

Alternatively, the expression level of a target gene may be determined through the microbeads method. For example, the expression levels of a plurality of target genes can be simultaneously determined through the following procedure. Specifically, probes for mRNA derived from different target genes are immobilized on microbeads which have been labeled with different fluorescent agents. The mRNA of the target genes prepared from a specimen (e.g., cultured cells, tissue, tissue section, or blood lysate) are hybridized therewith, and each target gene is specifically detected through the fluorescence therefrom. Also, a labeled probe is hybridized with mRNA of target genes which have hybridized with the probes immobilized on the microbeads, and the label of the probe is detected, to thereby determine the mRNA levels.

Furthermore, the copy number and the expression level of a target gene may be determined by use of the aforementioned probe through a known method (e.g., the southern hybridization method, the northern hybridization method, the FISH method, or the CGH method). In the case where a polypeptide encoded by the target gene is measured, the expression level of the target gene may be determined through a known immunostaining method (the ELISA method, the western blotting method, the EIA method, the RIA method, the IHC method, or the like) employing an antibody specific to the polypeptide.

In determination of the sensitivity of a subject to irinotecan, SN-38, and/or a salt thereof, the expression levels of the target genes in a biosample derived from a cancer patient before and during administration of an anticancer agent are measured, and the best tumor response rate (%), overall survival (days), or progression-free survival (days) of the cancer patient is calculated by any of the formulas (1) to (3). When the obtained value is equal to or higher than a predetermined reference value, the cancer has sensitivity to the anticancer agent, whereas when the obtained value is lower than the reference value, the cancer has no sensitivity to the anticancer agent. The predetermined reference value may be appropriately modified in accordance with the conditions and cancer type of the cancer patient, the type of a drug employed in combination with irinotecan, SN-38, and/or a salt thereof, etc. (see the Examples hereinbelow). In the case of sole administration of irinotecan, for example, the reference value of the best tumor response rate (%) is preferably 50%, the overall survival (days) 400 days, and the progression-free survival (days) 100 days.

When the value obtained by any of the formulas (1) to (3) is lower than the corresponding reference value before administration of an anticancer agent, the cancer can be found to have no sensitivity to irinotecan, SN-38, and/or a salt thereof. Thus, the effect of the agent is not expected. If such an ineffective anticancer agent is continuously administered to a cancer patient, progression of the cancer and aggravation of adverse effects may be anticipated. Thus, the sensitivity determination method of the present invention greatly contributes not only to determination of possible therapeutic response provided by an anticancer agent but also to prevention of aggravation of adverse effects which would otherwise be caused by continuous administration of an ineffective anticancer agent. Particularly, the sensitivity determination method of the present invention can be suitably applied to a cancer patient before administration of an anticancer agent. In addition, the method can also be employed as a method for selecting a patient who is expected to be treated by an anticancer agent.

Through measuring the expression levels of the target genes of a biosample derived from a cancer patient who is currently receiving an anticancer agent and monitoring the values obtained from the formulas (1) to (3) at every therapy cycle, the sensitivity of the cancer to the anticancer agent can be evaluated with time, whereby the method may also serve as a method for determining whether or not the therapy is to be continued. When the cancer has no sensitivity to the anticancer agent, a pharmaceutical effect of the agent is no longer expected, and only adverse effects of the anticancer agent are conceivably provided. Thus, the sensitivity determination method of the present invention may also be employed for preventing onset of undesired adverse effects and progression of cancer and aggravation of adverse effects which would otherwise be caused by continuation of ineffective therapy.

In addition to best tumor response rate (%), overall survival (days), and progression-free survival (days), examples of the parameter which may be employed for the sensitivity determination include efficacy-related parameters such as duration of overall response (days), duration of stable disease (days), and time to treatment failure (days); and adverse effect-related parameters such as blood concentration, elimination half-life, bioavailability, area under the blood concentration time curve (AUC), clearance, distribution volume, etc. of irinotecan, SN-38, and a metabolite thereof.

The method of the present invention may also be carried out by means of a kit for carrying out the method; i.e., a sensitivity determination kit. The sensitivity determination kit contains (A) assay reagents for measuring the expression levels of the seven genes, and (B) a protocol for calculating the best tumor response rate (%), overall survival (days), or progression-free survival (days). One embodiment of the assay reagents for measuring the expression levels of the seven genes (A) contains (A1) a protocol in which a method for measuring the expression levels of the target genes is described, (A2) a reagent for measuring the expression levels of the target genes, and (A3) a DNA chip onto which a nucleic acid fragment which can specifically hybridize with mRNA of the target genes has been immobilized. One embodiment of the protocol (B) contains (B1) a protocol for calculating the best tumor response rate (%), overall survival (days), or progression-free survival (days) from the formulas (1) to (3) and (B2) reference values for determining whether or not a subject has sensitivity to irinotecan, SN-38, and/or a salt thereof. The reference includes reference values of the best tumor response rate (%), overall survival (days), and progression-free survival (days), factors which cause variation in reference values, and the degree of the variation. These reference values may be appropriately predetermined in accordance with the conditions and cancer type of the cancer patient, the type of a drug employed in combination with irinotecan, SN-38, and/or a salt thereof, etc. With reference to the reference values, the aforementioned determination can be carried out.

The kit of the present invention is not limited to the above embodiment and encompasses a kit including all or a part of the members required for carrying out all or a part of the steps of the method. Examples of members required for carrying out the steps include a buffer.

By employing, as an index, an increase in any one of the best tumor response rate (%), overall survival (days), or progression-free survival (days) obtained from the formulas (1) to (3), a sensitivity-enhancing agent to irinotecan, SN-38, and/or a salt thereof can be selected through screening. In other words, the substance which increases these values in vitro or in vivo enhances sensitivity of a subject to an anticancer agent. In a cancer animal, the substance which increases these values before and after administration of an anticancer agent is defined as a substance which enhances the sensitivity to the anticancer agent (anticancer agent sensitivity-enhancing agent). In various cancer cell lines, the substance which increases these values in vitro in the presence of irinotecan, SN-38, and/or a salt thereof is defined as a substance which enhances the sensitivity to the anticancer agent (anticancer agent sensitivity-enhancing agent). When an anticancer agent sensitivity-enhancing agent is used, an increase in the value is observed before observation of regression of the tumor or cytocidal effect. Therefore, whether or not the test substance can serve as a useful anticancer agent sensitivity-enhancing agent can be determined in a shorter period of time, whereby load and cost involved in screening can be reduced, which is a great advantage of the present invention.

Through employment of the thus-obtained anticancer agent sensitivity-enhancing agent and irinotecan, SN-38, and/or a salt thereof (sensitivity enhancement target) in combination, the therapeutic effect of the anticancer agent can be remarkably enhanced. The composition of the present invention may be administered orally or parenterally, preferably parenterally. Upon administration, a composition containing an anticancer agent sensitivity-enhancing agent and an anticancer agent (sensitivity enhancement target) may be mixed with a solid or liquid non-toxic pharmaceutical carrier for providing a formulation suited for the administration route (oral, intrarectal, injection, etc.), to thereby form a general pharmaceutical preparation. The composition containing an anticancer agent sensitivity-enhancing agent and an anticancer agent (sensitivity enhancement target) may be a single composition containing both ingredients or a combination-type composition of two preparations. These ingredients may be administered through different routes.

Examples of the form of preparations include solid formulations such as tablet, granules, powder, and capsule; liquid preparations such as solution, suspension, and emulsion; and lyophilized formulations. These preparations may be produced through a method generally employed in the art. Examples of the non-toxic pharmaceutical carrier include starch, dextrin, fatty acid glyceride, polyethylene glycol, hydroxyethyl starch, ethylene glycol, polyoxyethylene sorbitan fatty acid ester, amino acid, gelatin, albumin, water, and physiological saline. If required, additives generally employed in the art such as a stabilizer, a humectant, an emulsifying agent, a binder, a tonicity agent, and a vehicle (diluent) may be appropriately added to the composition.

Note that the value of the first term and the factor of each gene expression level in each of the formulas (1) to (3) were determined from the data of gene expression levels obtained through real-time RT-PCR. However, if gene expression levels obtained through real-time RT-PCR have a certain correlation with those obtained through a method other than real-time RT-PCR, the value of the first term and the factor of each gene expression level in each of the formulas (1) to (3) may be modified with certain factors which adjust variations between real-time RT-PCR and a method other than real-time RT-PCR, and the thus-adjusted formulas may be used. In this case, gene expression levels determined through a method other than real-time RT-PCR are input into the relevant formula.

EXAMPLES

The present invention will next be described in more detail by way of examples, which should not be construed as limiting the invention thereto.

Example 1

Identification of Genes Relating to Sensitivity to SN-38 by Use of Cancer Cell Lines 1. Preparation of Total RNA from Human Cancer Cells and Cultured Human Non-Tumor Cells The employed cell lines are as follows: two human leukemia cell lines (myelogenous leukemia cell line K562 and acquired multidrug resistant cell line thereof K562/DOX); nine lung cancer cell lines (small-cell lung cancer cell line PC-6, acquired SN-38 resistant cell line thereof PC-6/SN2-5, acquired CPT-11 resistant cell line thereof PC-6/DQ2-2, lung adenocarcinoma cell line PC-9, acquired CDDP (cisplatin) resistant cell line thereof PC-9/CDDP, lung adenocarcinoma cell line PC-14, acquired CDDP resistant cell line thereof PC-14/CDDP, squamous cell lung cancer cell line LC-S, and lung adenocarcinoma cell line A549); seven digestive cancer cell lines (four colon cancer cell lines: HCC-48, HCC-50, COLO201, and COLO320DM, two gastric cancer cell lines: HSC-42 and MKN45, and one esophageal cancer cell line HEC-46); and one oral epithelium epidermal cancer cell line (KB). Total RNA was extracted from each cell line by means of RNeasy™ Mini kit (product of Qiagen) according to a protocol attached thereto, and stored at −80° C.

The quality of the extracted total RNA was confirmed by means of 2100 Bioanalyzer (product of Agilent Technologies) and RNA LabChip (product of Agilent Technologies). When the 18S rRNA peak and 28S rRNA peak were clear, the product was confirmed to be of high quality and then subjected to microarray analysis.

2. Comprehensive Gene Expression Analysis by Means of a Microarray and Quantitative Gene Expression Analysis Through Real-Time RT-PCR The above 19 cultured human tumor cell lines were analyzed in terms of gene expression profile by means of RIKEN human 21K array (containing 20,784 clones and positive and negative controls) and an oligonucleotide microarray, CodeLink™ Uniset Human 20K I Bioarray (product of GE Healthcare, containing 19,881 clones and positive and negative controls). For constructing RIKEN human 21K array, cDNA clones (glycerol stock) purchased from ResGen (Invitrogen Corp., Carlsbad, Calif.) were used as target DNA. In the cDNA microarray, COLO201 cells were employed as a reference sample, and poly(A) RNA of the sample cell line was labeled through reverse transcription by random priming with Cy5-dCTP and Cy3-dCTP. In the oligonucleotide microarray, all samples were labeled with Cy5 and evaluated through the single-color method. In the analysis by means of RIKEN human 21K array, a standardized relative expression level of each gene was obtained by determining $\log_2$ (Cy3/Cy5) of each spot and subtracting the median of $\log_2$ (Cy3/Cy5) signals of all the spots in the array from the signal of each spot. In oligonucleotide microarray analysis, the above-obtained signal intensity data were normalized by means of a microarray gene expression analysis software, GeneSpring™ GX (product of Agilent). Specifically, a standardized relative expression level of each gene was obtained by subtracting a background signal from a spot signal (when the obtained value was less than 0.01, 0.01 was employed) and dividing the thus-processed signal value by the median of signals of all the spots in the array. Also, the gene expression levels were quantitatively evaluated by means of TaqMan™ Gene Expression Assays (product of Applied Biosystems) and ABI Prism 7900HT sequence detection system (product of Applied Biosystems).

3. Evaluation of Sensitivity to Irinotecan and SN-38

The sensitivity, to irinotecan and SN-38, of the 19 cultured human tumor cell lines which had been subjected to comprehensive gene expression analysis was determined through the MTT (methylthiazol tetrazolium bromide) method. Specifically, $4 \times 10^3$ cells/well of each cell line and 80 µL/well of culture medium (10% fetal serum-added RPMI1640 medium) were added to each well of a 96-well microplate (Nunclon; Nunc, Roskilde, Denmark), and culturing was performed for 24 hours in an incubator at 37° C. under 5% $CO_2$. Thereafter, the culture medium (10% fetal serum-added RPMI1640 medium) was renewed, and SN-38 or irinotecan was added thereto at various concentrations. Culturing was further performed for 72 hours in an incubator at 37° C. under 5% $CO_2$. After completion of this culturing, the culture medium was removed, and PBS (phosphate buffer) was added at 100 μL/well, followed by centrifugation at 1,500 rpm for 5 minutes. The supernatant was removed through suction. Then, 0.4% MTT reagent (10 μL/well) and 0.1 M sodium succinate (10 μL/well) were added to the well, and culturing was performed for 2 hours at 37° C. under 5% $CO_2$. Subsequently, DMSO (150 μL) was added to the well, and pipetting was sufficiently performed. By means of a microplate reader (Maxline Microplate Reader, Molecular Devices, Sunnyvale, Calif.), absorbance at 570 to 650 nm was measured. An average absorbance of wells of culture medium was subtracted from the absorbance of each well of the drug-treatment group, and the obtained values of the wells were averaged. Similarly, the average absorbance of wells of culture medium was subtracted from the absorbance of each well of the control group (non-drug-treatment group), and the obtained values of the wells were averaged. The value of the drug-treatment group was divided by that of the control group, and the ratio is multiplied by 100, to thereby obtain percent growth inhibition (%). The data were plotted with respect to concentration in a semilog graph, to thereby draw a growth inhibition curve, through which a 50% growth inhibitory concentration ($IC_{50}$) was obtained. $IC_{50}$ was employed as a sensitivity index (Table 1).

TABLE 1

50% Growth inhibitory concentration ($IC_{50}$) determined by MTT method

| | $IC_{50}$(ng/mL) | |
|---|---|---|
| | Irinotecan | SN-38 |
| KB | 2234 | 5.26 |
| MKN45 | 809 | 2.60 |
| K562 | 2303 | 2.84 |
| HCC-48 | 1111 | 1.99 |
| HEC-46 | 7786 | 34.82 |
| HCC-50 | 5105 | 22.27 |
| HSC-42 | 743 | 2.81 |
| K562/DOX | 3933 | 4.10 |
| COLO201 | 979 | 2.84 |
| COLO320DM | 1777 | 3.43 |
| PC-6 | 691 | 2.91 |
| PC-6/DQ2-2 | 4256 | 97.35 |
| PC-6/SN2-5 | 2853 | 24.40 |
| PC-9 | 2752 | 8.17 |
| PC-9/CDDP | 2679 | 9.05 |
| PC-14 | 4666 | 11.16 |
| PC-14/CDDP | 4025 | 6.26 |
| LC-S | 18880 | 137.07 |
| A549 | 5631 | 25.23 |

4. Identification of Genes Relating to Sensitivity to SN-38

From the aforementioned 19 cell lines, genes exhibiting an expression level correlated with sensitivity to an anticancer agent (irinotecan or SN-38), which were obtained through the cDNA microarray analysis and the oligonucleotide microarray analysis with rank correlation analysis, were extracted as candidate genes which relate to the sensitivity to irinotecan, SN-38, and/or a salt thereof. Specifically, the relative expression levels of all the genes which had been subjected to both microarray analyses and the 50% growth inhibitory concentrations ($IC_{50}$) of irinotecan or SN-38 obtained through the MTT method were ranked, respectively. A gene having a positive or negative correlation with the relative expression level and $IC_{50}$ of irinotecan and/or SN-38 was extracted as a candidate gene which relates to the sensitivity to irinotecan, SN-38, and/or a salt thereof. In addition, among genes indicated to have a certain correlation between the rank in the relative expression level obtained by RIKEN human 21K array (20,784 probes) and the rank in $IC_{50}$ value (P<0.1), genes whose relation to sensitivity of tumor cells to irinotecan, SN-38, and/or a salt thereof was previously reported by two or more different institutions in 897 papers recorded in the National Library of Medicine's Pubmed (1996 to 2005) and whose contribution to the sensitivity was functionally confirmed through a gene transfer experiment, a knock down experiment, etc. were extracted as known sensitivity-related candidate genes. Also, regardless of the existence of a previous report, genes indicated to have a high correlation in rank correlation analysis between both of the relative expression level obtained by RIKEN human 21K array and by CodeLink™ UniSet Human 20K I Bioarray, and the both $IC_{50}$ value of irinotecan and SN-38 (P<0.01) were extracted as novel sensitivity-related candidate genes. In terms of the candidate genes, quantitative gene expression analysis of the 19 cell lines was performed through real-time RT-PCR employing TaqMan™ Gene Expression Assays (product of Applied Biosystems). Finally, genes exhibiting reproducibility (P<0.05) in correlation (linear regression analysis) between the expression levels and $IC_{50}$ values were identified as irinotecan-sensitivity-related genes and SN-38-sensitivity-related genes (12 genes: 5 known genes and 7 novel genes) (Tables 2 and 3). None of the thus-identified 7 novel genes has been reported to involve the sensitivity of tumor cells to irinotecan or SN-38.

TABLE 2

Genes which exhibited expression levels rank-correlated with the sensitivity to irinotecan or SN-38 (P < 0.1) in cDNA microarray analysis and in which the correlation was reproduced in expression levels determined through real-time RT-PCR

| | Irinotecan R | | SN-38 R | |
|---|---|---|---|---|
| | cDNA microarray analysis | Real-time RT-PCR analysis | cDNA microarray analysis | Real-time RT-PCR analysis |
| ABCG2 | | | 0.639** | 0.845*** |
| CYP3A4 | | 0.819*** | 0.437* | 0.716*** |
| MGMT | 0.579** | 0.753*** | 0.461* | 0.619*** |
| POR | 0.441* | 0.893*** | | 0.785*** |
| TOP2A | | | 0.426* | 0.775*** |

*0.05 <= P < 0.1;
**0.01 <= P < 0.05
***P < 0.01

TABLE 3

Genes which exhibited expression levels rank-correlated with the sensitivity to irinotecan or SN-38 (P < 0 .01) in cDNA microarray analysis and in oligonucleotide microarray analysis

| | R | |
|---|---|---|
| | cDNA microarray analysis | Oligonucleotide microarray analysis |
| AMD1 | −0.659*** | −0.586*** |
| CTSC | −0.754*** | −0.698*** |
| EIF1AX | −0.626*** | −0.626*** |
| C12orf30 | −0.624*** | −0.589*** |
| DDX54 | −0.652*** | −0.621*** |

TABLE 3-continued

Genes which exhibited expression levels rank-correlated with
the sensitivity to irinotecan or SN-38 (P < 0.01)
in cDNA microarray analysis and
in oligonucleotide microarray analysis

| | R | |
|---|---|---|
| | cDNA microarray analysis | Oligonucleotide microarray analysis |
| PTPN2 | −0.628*** | −0.696*** |
| TBX3 | −0.623*** | −0.619*** |

*0.05 < = P < 0.1;
**0.01 < = P < 0.05;
***P < 0.01

5. Establishment of In Vitro Efficacy-Predicting Formula Employing Extracted Known and Novel SN-38-Sensitivity-Related Genes Although all the thus-extracted genes exhibited high correlation between the determined expression levels and $IC_{50}$ values, the drug sensitivity mechanism of cells is known to be a complex system involving a number of factors. Thus, efficacy-predicting formulas were prepared through multiple regression analysis employing determined expression levels of the identified genes, and the predictability of each formula was confirmed. As a result, there were established a predicting formula employing the expression levels of 5 known genes ([ABCG2], [CYP3A4], [MGMT], [POR], and [TOP2A]):

$$\ln [IC_{50}] = 8.5945 + 0.0627 \ln [ABCG2] + 0.0219 \ln [CYP3A4] + 0.0299 \ln [MGMT] - 0.5849 \ln [POR] + 0.8099 \ln [TOP2A] \quad (4),$$

and a predicting formula employing the expression levels of 7 novel genes ([AMD1], [CTSC], [EIF1AX], [C12orf30], [DDX54], [PTPN2], and [TBX3]):

$$\ln [IC_{50}] = 6.2118 + 0.4942 \ln [AMD1] - 0.3801 \ln [CTSC] + 0.3782 \ln [EIF1AX] - 0.4903 \ln [C12orf30] + 1.1019 \ln [DDX54] - 1.2042 \ln [PTPN2] - 0.1967 \ln [TBX3] \quad (5).$$

The two formulas were indicated to have high predictability (R=0.7677, AICPS (Akaike's information criterion per sample)=−1.086 in formula (4), and R=0.8442, AICPS=−1.523 in formula (5)) (FIG. 1).

Example 2

Clinical Test of Human Subjects Under Sole Administration of CPT-11

1. Clinical Test of Human Subjects Under Sole Administration of CPT-11

The aforementioned studies have revealed that the efficacy of SN-38 is possibly predicted from the aforementioned known and novel genes identified in cultured human tumor cell lines and efficacy predicting formulas employing the expression levels of the genes. In order to clarify the possibility of efficacy prediction employing the genes in clinical settings, prospective genomic pharmacological clinical studies were carried out. The target cases were unresectable stage 1V colorectal cancer patients who had not received chemotherapy and from whom a tumor specimen could be removed during palliative surgery. The selection criteria for the test human subjects were as follows: (1) a case which was histologically diagnosed as colorectal cancer; (2) a case which underwent surgery of unresectable stage 1V colorectal cancer; (3) a case involving response evaluation criteria in solid tumors (RECIST); and (4) a case where physiological functions (bone marrow, liver, kidney, heart, etc.) are sufficiently maintained, wherein the blood test results within one week before preliminary registration or registration fell within the following reference ranges: WBC: 4,000 μL to 12,000/μL, NEUT: 2,000 μL, PLT: ≥100,000/μL, Hb: 9.0 g/dL, GOT.GPT: less than twice the upper limit of normal at the institution (in the case of liver metastasis, less than three times), T-Bil: ≤1.5 mg/dL, Cr: ≤0.5 mg/dL, CCr: ≥50 mL/min, BUN: ≤25 mg/dL, and CRP ≤1 mg/dL. The test human subjects also included a case classified in performance status (Eastern Cooperative Oncology Group: ECOG) of 0 to 2; a case which underwent no preliminary treatment other than surgery; a case for which, at registration, 21 days or longer had passed after surgery; a case which is expected to have a predicted survival period of 3 months or longer; a case which has no severe co-morbidity or active multiple primary cancer; a case of an age of 20 or older and younger than 75; a case from which a tissue sample for gene analysis was obtained at surgery; and a case where a patient himself or herself provided informed consent of surgery including donation of a biosample for studies. Excluded were the following cases: (1) a case having a severe complication; (2) a case having an infectious complication; (3) a case having diarrhea (watery stools); (4) a case having intestinal paralysis, ileus, or subileus (only before registration); (5) a case having interstitial pneumonia or pulmonary fibrosis; (6) a case having ascites or pleural fluid in a large volume; (7) a case having jaundice; (8) a case having a heart disease such as ischemic heart disease or arrythmia to an extent requiring treatment (a case having left ventricular hypertrophy or slight left ventricular overload concomitant with hypertension or slight right bundle branch block may be registered); (9) a case which experienced myocardial infarction within 6 months; (10) a case having cirrhosis as a complication; (11) a case exhibiting fresh hemorrhage from the digestive tract to be treated by repeated blood transfusion; (12) a case having a mental disorder treated with or possibly to be treated with a psychotropic; (13) a case having difficult-to-control diabetes as a complication; (14) a case having other severe post-operative complications; (15) a case experienced severe anaphylaxis to other drugs; (16) a female subject in pregnancy or lactation or a male or female subject wishing to have a baby; and (17) a case which is positive to hepatitis virus, HIV virus, or syphilis. CPT-11 was administered solely. After passage of a period of 21 days or longer from surgery, administration was started. From day 1 (administration starting day), CPT-11 was administered once a week for three weeks followed by a one-week rest period (1 course). The dose of CPT-11 was 60 to 100 mg/m². Forty-four subjects in total participated in the study, and the best tumor response rate (%), progression-free survival (days), and overall survival (days) could be evaluated in all the participants. Quantitative expression levels of the above-identified 5 known and 7 novel irinotecan-sensitivity-related or SN-38-sensitivity-related genes were analyzed through real-time RT-PCR employing TaqMan™ Gene Expression Assays. Except for one case in which extraction of RNA was not completed, the expression levels were quantitated in 43 cases.

2. Establishment of Efficacy-Predicting Formulas and Validity Thereof.

Efficacy predicting formulas were established from the expression levels of 5 known genes and 7 novel genes of the above-registered 43 cases, and the validity of the formulas was evaluated (FIGS. 2, 3, 4, 5, 6, and 7). Regarding the best tumor response rate (%), 36 cases were employed in the efficacy prediction study, and the remaining 7 cases were not employed, since they were diagnosed as progressive disease (PD) due to appearance of a new lesion. The 36 cases were divided at random into a group of 20 cases for establishment of predicting formulas and the other group of 16 cases for evaluation of the predicting formulas. Similarly, regarding the progression-free survival (days), 26 cases were employed in the efficacy prediction study, and the remaining cases were not employed (8 cases: stop of therapy due to toxicity, 4 cases: change of the therapy method requested by patients, 4 cases: performing radical surgery, and 1 case: complete response (CR)). The 26 cases were divided into a group of 16 cases for establishment of predicting formulas and the other group of 10 cases for evaluation of the predicting formulas. Regarding the overall survival (days), 28 cases which had finished the survival periods were employed in the efficacy prediction study, and the remaining 15 living cases were not employed. The 28 cases were divided into a group of 15 cases for establishment of predicting formulas and the other group of 13 cases for evaluation of the predicting formulas. The predicting formulas were established in a manner similar to that employed in in vitro studies. As a result, there were established predicting formulas employing the expression levels of 5 known genes ([ABCG2], [CYP3A4], [MGMT], [POR], and [TOP2A]):

Best tumor response rate (ratio to tumor diameter baseline, %)=91.287+10.472[*ABCG2*]+0.65518[*CYP3A4*]−3.8065[*MGMT*]−2.1487[*POR*]+17.354[*TOP2A*]   (6)

(R=0.7393, AICPS=5.188021),

Progression-free survival (days)=69.568−51.615[*ABCG2*]−3.1043[*CYP3A4*]+15.985[*MGMT*]+107.90[*POR*]−187.63[*TOP2A*]   (7)

(R=0.8382, AICPS=8.073506), and

Overall survival (days)=425.67+363.52[*ABCG2*]−2.8749[*CYP3A4*]+20.765[*MGMT*]−481.61[*POR*]+321.70[*TOP2A*]   (8)

(R=0.9267, AICPS=9.155001), and predicting formulas employing the expression levels of 7 novel genes ([AMD1], [CTSC], [EIF1AX], [C12orf30], [DDX54], [PTPN2], and [TBX3]):

Best tumor response rate (%)=139.49−12.089×$A$−84.477×$B$−12.737×$C$+85.900×$D$−29.119×$E$−6.8630×$F$+20.303×$G$   (1);

(R=0.9420, AICPS=5.460938),

Overall survival (days)=512.78−192.11×$A$−120.78×$B$+134.53×$C$−11.883×$D$+157.24×$E$+31.962×$F$−386.55×$G$   (2); and (R=0.7103, AICPS=8.411958), and Progression-free survival (days)=68.076+78.277×$A$−57.358×$B$−15.011×$C$+8.9798×$D$+73.077×$E$−38.961×$F$−43.313×$G$   (3)

(R=0.8426, AICPS=10.20386).

The aforementioned predicting formulas were evaluated in validity. The evaluation has revealed that none of the predicting formulas employing the expression levels of 5 known genes can predict any effectiveness (efficacy) parameter [Best tumor response rate (ratio to tumor diameter baseline, %), P=0.2079, R=−0.3450; progression-free survival (days), P=0.4802, R=0.2712, and overall survival (days), P=0.4639, R=−0.2316]. In contrast, the evaluation has revealed that the predicting formulas employing the expression levels of 7 novel genes have high predictability in any effectiveness (efficacy) parameter, particularly best tumor response rate (ratio to tumor diameter baseline, %) and overall survival (days) [Best tumor response rate (ratio to tumor diameter baseline, %), P=0.007, R=0.6491; progression-free survival (days), P=0.1124, R=0.5333; and overall survival (days), P=0.0114, R=0.6749].

4. Prediction of Effectiveness (Efficacy) by Specific Single Gene

The predicting formulas employing the expression levels of the identified 7 novel genes have been found to be useful. Thus, whether or not employment of each of the identified genes solely can predict the efficacy was investigated through linear regression analysis. As a result, the respective expression levels of the 5 known genes and 7 novel genes were not correlated with any effectiveness (efficacy) parameter, and the prediction by sole use of the expression level of each gene would be difficult. Table 4 shows the relationship between the expression level of each of the 5 known genes (ABCG2, CYP3A4, MGMT, POR, and TOP2A) and the best tumor response rate (%), progression-free survival (days), and overall survival (days).

TABLE 4

| | Best tumor response rate (%) | | Progression-free survival (days) | | Overall survival (days) | |
|---|---|---|---|---|---|---|
| | R | P | R | P | R | P |
| ABCG2 | −0.1719 | 0.3234 | 0.0265 | 0.8999 | −0.0771 | 0.7024 |
| CYP3A4 | −0.1097 | 0.5304 | 0.0855 | 0.6843 | 0.1657 | 0.4089 |
| MGMT | 0.2720 | 0.1139 | 0.3166 | 0.1231 | −0.2184 | 0.2738 |
| POR | −0.0525 | 0.7645 | 0.0424 | 0.8404 | −0.1305 | 0.5163 |
| TOP2A | 0.1414 | 0.4179 | −0.2325 | 0.2634 | −0.1960 | 0.3271 |

Also, Table 5 shows the relationship between the expression level of each of the 7 novel genes (AMD1, CTSC, EIF1AX, C12orf30, DDX54, PTPN2, and TBX3) and the best tumor response rate (%), progression-free survival (days), and overall survival (days).

TABLE 5

| | Best tumor response rate (%) | | Progression-free survival (days) | | Overall survival (days) | |
|---|---|---|---|---|---|---|
| | R | P | R | P | R | P |
| AMD1 | 0.1002 | 0.5667 | 0.2015 | 0.3341 | −0.4387 | 0.0221 |
| CTSC | 0.0800 | 0.6477 | −0.0866 | 0.6806 | −0.5649 | 0.0021 |
| EIF1AX | −0.3055 | 0.0744 | 0.1900 | 0.3631 | −0.2383 | 0.2314 |
| C12orf30 | 0.2509 | 0.1460 | −0.0377 | 0.8580 | −0.3791 | 0.0511 |
| DDX54 | 0.1108 | 0.5264 | 0.3909 | 0.0534 | −0.4136 | 0.0320 |
| PTPN2 | 0.0875 | 0.6171 | 0.2269 | 0.2754 | −0.2519 | 0.2049 |
| TOP2A | 0.1061 | 0.5440 | 0.2216 | 0.2871 | −0.4504 | 0.0184 |

As described hereinabove, only the predicting formulas (1) to (3) employing the expression levels of the thus-identified 7 novel genes are found to be useful for predicting the best tumor response rate (%), progression-free survival (days), and overall survival (days), which are parameters for therapeutic response (efficacy) of irinotecan, SN-38, and/or a salt thereof.

The invention claimed is:

1. A method for treating cancer in a human subject, comprising:
   (i) measuring a pre-treatment mRNA expression level of the AMD1 gene, CTSC gene, EIF1AX gene, C12orf30 gene, DDX54 gene, PTPN2 gene, and TBX3 gene in a biosample derived from a subject having colorectal cancer;
   (ii) calculating, using the measured pre-treatment mRNA expression level, a pre-treatment value of the best tumor response rate using formula (1) wherein:

the best tumor response rate, in percentage=139.49−12.089×$A$−84.477×$B$−12.737×$C$+85.900×$D$−29.119×$E$−6.8630×$F$+20.303×$G$    formula (1) is:

wherein
   A represents an expression level of the AMD1 gene,
   B represents an expression level of the CTSC gene,
   C represents an expression level of the EIF1AX gene,
   D represents an expression level of the C12orf30 gene,
   E represents an expression level of the DDX54 gene,
   F represents an expression level of the PTPN2 gene, and
   G represents an expression level of the TBX3 gene;
   (iii) administering to the subject at least one of irinotecan, SN-38, a salt of irinotecan, and a salt of SN-38;
   (iv) measuring a post-treatment mRNA expression level of the AMD1 gene, CTSC gene, EIF1AX gene, C12orf30 gene, DDX54 gene, PTPN2 gene, and TBX3 gene in a biosample derived from the subject;
   (v) calculating, using the measured post-treatment mRNA expression level, a post-treatment value of the best tumor response rate using formula (1);
   (vi) comparing the pre-treatment value calculated in (ii) with the post-treatment value calculated in (v); and
   (vii) continuing the administering of said at least one of irinotecan, SN-38, a salt of irinotecan, and a salt of SN-38 when the value post-treatment value calculated in (v) is equal to or higher than the pre-treatment value calculated in (ii); or halting the administering of said at least one of irinotecan, SN-38, a salt of irinotecan, and a salt of SN-38 when the post-treatment value calculated in (v) is lower than the pre-treatment value calculated in (ii).

2. A method for treating cancer in a human subject, comprising:
   (i) measuring a pre-treatment mRNA expression level of the AMD1 gene, CTSC gene, EIF1AX gene, C12orf30 gene, DDX54 gene, PTPN2 gene, and TBX3 gene in a biosample derived from a subject having colorectal cancer;
   (ii) calculating, using the measured pre-treatment mRNA expression level, a pre-treatment value of overall survival using formula (2), wherein:

overall survival, in days=512.78−192.11×$A$−120.78×$B$+134.53×$C$−11.883×$D$+157.24×$E$+31.962×$F$−386.55×$G$,    formula (2) is:

wherein
   A represents an expression level of the AMD1 gene,
   B represents an expression level of the CTSC gene,
   C represents an expression level of the EIF1AX gene,
   D represents an expression level of the C12orf30 gene,
   E represents an expression level of the DDX54 gene,
   F represents an expression level of the PTPN2 gene,
   G represents an expression level of the TBX3 gene;
   (iii) administering to the subject at least one of irinotecan, SN-38, a salt of irinotecan, and a salt of SN-38;
   (iv) measuring a post-treatment mRNA expression level of the AMD1 gene, CTSC gene, EIF1AX gene, C12orf30 gene, DDX54 gene, PTPN2 gene, and TBX3 gene in a biosample derived from the subject;
   (v) calculating, using the measured post-treatment mRNA expression level, a post-treatment value of overall survival using formula (2);
   (vi) comparing the pre-treatment value calculated in (ii) with the post-treatment value calculated in (v); and
   (vii) continuing the administering of said at least one of irinotecan, SN-38, a salt of irinotecan, and a salt of SN-38 when the post-treatment value calculated in (v) is equal to or higher than the pre-treatment value calculated in (ii); or halting the administering of said at least one of irinotecan, SN-38, a salt of irinotecan, and a salt of SN-38 when the post-treatment value calculated in (v) is lower than the pre-treatment value calculated in (ii).

3. A method for treating cancer in a human subject, comprising:
   (i) measuring a pre-treatment mRNA expression level of the AMD1 gene, CTSC gene, EIF1AX gene, C12orf30 gene, DDX54 gene, PTPN2 gene, and TBX3 gene in a biosample derived from a subject having colorectal cancer;
   (ii) calculating, using the measured pre-treatment mRNA expression level, a pre-treatment value of progression-free survival using formula (3), wherein:

progression-free survival, in days=68.076+78.277×$A$−57.358×$B$−15.011×$C$+8.9798×$D$+73.077×$E$−38.961×$F$−43.313×$G$,    formula (3) is:

wherein
   A represents an expression level of the AMD1 gene,
   B represents an expression level of the CTSC gene,
   C represents an expression level of the EIF1AX gene,
   D represents an expression level of the C12orf30 gene,
   E represents an expression level of the DDX54 gene,
   F represents an expression level of the PTPN2 gene,
   G represents an expression level of the TBX3 gene;
   (iii) administering to the subject at least one of irinotecan, SN-38, a salt of irinotecan, and a salt of SN-38;

(iv) measuring a post-treatment mRNA expression level of the AMD1 gene, CTSC gene, EIF1AX gene, C12orf30 gene, DDX54 gene, PTPN2 gene, and TBX3 gene in a biosample derived from the subject;
(v) calculating, using the measured post-treatment mRNA expression level, a post-treatment value of progression-free survival using formula (3),
(vi) comparing the pre-treatment value calculated in (ii) with the post-treatment value calculated in (v); and
(vii) continuing the administering of said at least one of irinotecan, SN-38, a salt of irinotecan, and a salt of SN-38 when the post-treatment value calculated in (v) is equal to or higher the pre-treatment value calculated in (ii); or halting the administering of said at least one of irinotecan, SN-38, a salt of irinotecan, and a salt of SN-38 when the post-treatment value calculated in (v) is lower than the pre-treatment value calculated in (ii).

4. The method of claim 1, 2, or 3, wherein the human subject is treated with irinotecan.

5. The method of claim 1, 2, or 3, wherein the human subject is treated with SN-38.

6. The method of claim 1, 2, or 3, wherein the human subject is treated with a salt of irinotecan.

7. The method of claim 1, 2, or 3, wherein the human subject is treated with a salt of SN-38.

* * * * *

SEQUENCE LISTING

<160> NUMBER OF SEQ ID NOS: 1

<210> SEQ ID NO 1
<211> LENGTH: 30
<212> TYPE: DNA
<213> ORGANISM: Homo sapiens

<400> SEQUENCE: 1
gcatgtgagt gttccgactt catctgttcc                                      30